(12) United States Patent
Warrington et al.

(10) Patent No.: US 7,241,454 B2
(45) Date of Patent: Jul. 10, 2007

(54) PESTICIDAL FORMULATIONS

(75) Inventors: Roger Paul Warrington, Berkshire (GB); John Henry Nettleton-Hammond, Berkshire (GB)

(73) Assignee: Syngenta Limited, Guildford, Surrey (GB)

( * ) Notice: Subject to any disclaimer, the term of this patent is extended or adjusted under 35 U.S.C. 154(b) by 127 days.

(21) Appl. No.: 10/363,013

(22) PCT Filed: Aug. 21, 2001

(86) PCT No.: PCT/GB01/03742

§ 371 (c)(1),
(2), (4) Date: Jul. 14, 2003

(87) PCT Pub. No.: WO02/19821

PCT Pub. Date: Mar. 14, 2002

(65) Prior Publication Data

US 2004/0014800 A1    Jan. 22, 2004

(30) Foreign Application Priority Data

Sep. 5, 2000 (GB) ................................. 0021786.9

(51) Int. Cl.
*A01N 25/00* (2006.01)
*A61K 31/44* (2006.01)

(52) U.S. Cl. ...................... 424/405; 514/345

(58) Field of Classification Search ................. 514/345; 424/405

See application file for complete search history.

(56) References Cited

U.S. PATENT DOCUMENTS 5,674,517 A * 10/1997 Carpenter .................. 424/405
5,948,805 A * 9/1999 Geddens et al. ............ 514/376
6,277,858 B1 * 8/2001 Walter ...................... 514/260.1
6,677,399 B2 * 1/2004 Herbert et al. ............. 524/547

FOREIGN PATENT DOCUMENTS

| EP | 0951831 | 10/1999 |
| EP | 1023832 | 8/2000 |
| WO | 0008931 | 2/2000 |
| WO | WO-00/08931 | * 2/2000 |

OTHER PUBLICATIONS

S. Haas, H.W. Hasslin & C. Schlatter, "Influence of Polymeric Surfactants on Pesticidal Suspension Concentrates: Dispersing Ability, Milling Efficiency and Stabilization Power," Colloids Surf., No. 183-185, 2001, pp. 785-793.

* cited by examiner

*Primary Examiner*—Alton Pryor
(74) *Attorney, Agent, or Firm*—Syngenta Crop Protection; Rebecca A. Gegick

(57) ABSTRACT

Aqueous pesticidal suspensions comprise: (a) 5 to 40% w/v of (i) a pesticide having a melting point in the range of from 50 to 120° C. and a solubility in water of not more than 0.2% w/v or (ii) a mixture of the pesticide (i) and one or more other pesticides having a melting point of at least 50° C. and a solubility in water of not more than 0.2% w/v in the ratio of at least 1 part by weight of the pesticide (i) to 10 parts by weight of the other pesticide or pesticides, (b) 2.5 to 20% w/v of a non-ionic alkoxylate surfactant, (c) 0.5 to 5% w/v of a naphtalene sulphonate-formaldehyde condensate, (d) 0.1 to 5% w/v of a non-ionic polymethyl methacrylate-polyethylene oxide graft copolymer, (e) 0 to 25% w/v of other additives, and (f) water in sufficient amount to bring the total composition to 100% w/v. Pesticidal suspensions formulated in this way show less variation in viscosity than hitherto.

14 Claims, No Drawings

PESTICIDAL FORMULATIONS

This invention relates to pesticidal formulations and, more particularly, to aqueous suspensions of pesticides and of pesticide mixtures.

A pesticide which has a reasonably high melting point, a low solubility in water and which is chemically stable in water is conveniently marketed in the form of an aqueous suspension concentrate (SC). SCs are diluted when applied to plants, but marketing them in concentrated form enables transport costs to be kept to a minimum.

Aqueous SCs may be prepared by bead milling the solid pesticide in water, optionally with one or more dispersing agents, (the "premix") to produce a fine aqueous suspension (the "mill base"). One or more wetting agents may be included along with one or more suspending agents (or anti-settling agents) to reduce the rate at which the milled particles settle. Bioenhancing adjuvants to increase the bio-efficacy of, particularly, fungicides, and preservatives, anti-foams, antifreezes and other agents may also be included. These concentrates are often required to withstand storage for prolonged periods and then be capable of further dilution to form aqueous preparations which remain homogeneous for a sufficient time to enable them to be applied by conventional spray equipment.

Particularly suitable dispersing agents for use in SCs are the group of anionic dispersing agents known as naphthalene sulphonate/formaldehyde condensates, and particularly suitable bioenhancing adjuvants are the large group of non-ionic ethoxylated surfactants, for example, ethoxylated sorbitan esters or fatty alcohols. Unfortunately, SCs prepared using these agents tend to vary in viscosity depending on the quality, in particular the impurity content, of the active ingredient and also on the extent of any interaction between the bioenhancing agent and dispersing agent. Inconsistencies in viscosity are commercially unacceptable, causing problems in formulating SCs and in handling and applying them. The object of the present invention is to provide an aqueous pesticidal SC of more consistent viscosity.

Thus according to the present invention there is provided an aqueous suspension of a pesticide which comprises:

a) 5 to 40% w/v of (i) a pesticide having a melting point in the range of from 50 to 120° C. and a solubility in water of not more than 0.2% w/v or (ii) a mixture of the pesticide (i) and one or more other pesticides having a melting point of at least 50° C. and a solubility in water of not more than 0.2% w/v in the ratio of at least 1 part by weight of the pesticide (i) to 10 parts by weight of the other pesticide or pesticides,
b) 2.5 to 20% w/v of a non-ionic alkoxylate surfactant,
c) 0.5 to 5% w/v of a naphthalene sulphonate-formaldehyde condensate,
d) 0.1 to 5% w/v of a non-ionic polymethyl methacrylate-polyethylene oxide graft copolymer,
e) 0 to 25% w/v of other additives, and
f) water in sufficient amount to bring the total composition to 100% w/v.

The abbreviation % w/v is used to mean the weight in grammes present in every 100 milliliters volume of the suspension.

Component (a) of the aqueous suspension consists of the pesticide (i) alone or a mixture of the pesticide (i) with one or more other pesticides. In either case it represents 5 to 40% w/v, suitably 20 to 30% w/v and typically approximately 25% w/v, of the total composition of the suspension.

Pesticides having a melting point below 50° C. do not lend themselves to being formulated as SCs by the bead milling process due to temperatures of 60° C. or higher being reached in an uncooled bead mill. With cooling, it may be possible to keep the mill temperature sufficiently low to mill pesticides having a melting point down to around 50° C.

The pesticide (i) will not normally have a melting point higher than 120° C. Inconsistencies in the viscosity of SC formulations of pesticides with melting points above this level are less marked and, therefore, there is less value in formulating pesticides with melting points this high using the present invention. The invention is of greater value when used with pesticides having a melting point in the range of from 55 to 110° C., preferably 60 to 100° C., more preferably 65 to 90° C. and especially 70 to 80° C.

Pesticides having a solubility in water of more than 0.2% w/v (2000 ppm) are not usually suitable for formulating as SCs. Normally, those suitable for use in the present invention will have a solubility of not more than 0.1% w/v, preferably less than 0.02% w/v and ideally less than 0.005% w/v.

Pesticides include herbicides, insecticides and fungicides. Examples of pesticides having a suitable melting point and a suitable level of water solubility for use in this invention are napropamide, haloxyfop, clodinafop-propargyl, cypermethrin, alpha-cypermethrin, beta-cypermethrin, cyproconazole, difenoconazole, hexaconazole, penconazole, tebuconazole, azoxystrobin, kresoxim-methyl, metominostrobin, picoxystrobin, pyraclostrobin, trifloxystrobin, cyprodinil, fluazinam and quinoxyfen. The invention is, however, particularly useful for fungicides, as a large number of these are sold as SCs. Fungicides, for which the invention is of special interest are the strobilurin fungicides and particularly picoxystrobin.

The other pesticide or pesticides which may be used in combination with the pesticide (i) in component (a) have a melting point of at least 50° C. and a solubility in water of not more than 0.2% w/v. While the lower melting point and solubility requirements are necessary for the optional pesticide or pesticides, for the same reasons as for the pesticide (i) discussed above, there is no need to impose an upper limit on their melting points.

Examples of suitable optional pesticides include those described above for the pesticide (i) and additionally, chlorothalonil, fludioxonil, epoxiconazole, paclobutrazol and thiabendazole, which have melting points above 120° C. The invention is particularly useful for fungicide mixtures, i.e. where the pesticide (i) and the other optional pesticide or pesticides are all fungicides. Of special interest are formulations in which the pesticide (i) is a strobilurin fungicide, for example picoxystrobin, and the other pesticide or pesticides are fungicides. Of even more interest are mixtures of picoxystrobin with a triazole fungicide such as hexaconazole or cyproconazole.

There should be used at least 1 part by weight of the pesticide (i) in combination with 10 parts by weight of the other pesticide or pesticides. Normally the weight ratio of the pesticide (i) to the other pesticide or pesticides will be in the range of 1:7.5 to 5:1, for example 1:2.5 to 3.5:1. Of particular interest is a mixture of pesticide (i) and another pesticide used in a weight ratio (pesticide (i): other pesticide) in the range 1:2.5 to 2.5:1, typically 1:1.

Component (b), which comprises 2.5 to 20% w/v, suitably 10 to 15% w/v, of the total composition will normally be present in approximately half the weight % of component (a). It may be any non-ionic alkoxylate (typically ethoxylate) surfactant. Thus it may be an aliphatic alcohol alkoxylate, for example, an aliphatic alcohol ethoxylate. For particular mention are alcohol ethoxylates prepared from saturated or unsaturated, linear or branched aliphatic alcohols having on average from 8 to 20 carbon atoms, and which contain from 5 to 25, typically from 10 to 20, ethylene oxide units per molecule. Ethoxylates favoured because of their biological enhancing effect, are those which contain from 8 to 18, for example from 12 to 18, carbon atoms in the alcohol moiety and 10 to 20 ethylene oxide units, ideally 17 carbon atoms and 17 ethylene oxide units. Such surfactants are commercially available and sold under trade marks such as Brij, Volpo, Arlasolve, Atphos, Synperonic and Lubrol, the name sometimes indicating the average number of carbon atoms in the alcohol and/or the average number of ethylene oxide units per molecule, for example, Lubrol 17A17. Other suitable ethoxylates include the condensation products of ethylene oxide with fatty alcohols such as oleyl or cetyl alcohol, with alkyl phenols such as octyl- or nonylphenol, octylcresol or tristyryl phenol, with amines, with castor oil and with esters. Of particular interest are the sorbitan ester ethoxylates (e.g. Tween 20). Other suitable ethoxylates include the ethyleneoxide/propylene oxide/ethylene oxide block copolymers sold, for example, under the trade mark Pluronic.

Component (c), which comprises 0.5 to 5% w/v, suitably 2 to 3% w/v, of the total composition will normally be present in approximately one tenth the weight % of component (a). It may be any naphthalene sulphonate-formaldehyde condensate and will usually be in the form of the sodium salt. An example of a suitable commercial product is Morwet D425.

Component (d), which comprises 0.1 to 5% w/v, for example 0.1 to 4.5% w/v, 0.1 to 4% w/v, 0.1 to 3% w/v, 0.1 to 2% w/v or 0.1 to 1% w/v, of the total composition need only be present in very small amounts to moderate the viscosity of the suspension. Thus an acceptable consistency of viscosity is obtained using amounts of 0.1 to 0.9%, preferably 0.1 to 0.5% w/v of component (d), typically 0.3 to 0.4% w/v. Any non-ionic polymethyl methacrylate-polyethylene oxide graft copolymer may be used. Suitably it has a molecular weight of 20,000 to 30,000. Of particular advantage is the product sold under the trade mark Atlox 4913. This product contains approximately one third of the ionic polymethyl methacrylate-polyethylene oxide graft copolymer, one third water and one third propylene glycol. Thus, typically, when Atlox 4913 is used it will form 1% w/v of the total composition—equivalent to 0.33% w/v of component (d).

Other additives which may be included as component (e) are, for example, antisettling or suspending agents, antifoaming agents, antifreezes and preservatives. Suitable suspending agents, typically used in amounts of from 1 to 5% w/v, are hydrophilic colloids (for example, polyvinylpyrrolidone, sodium carboxymethylcellulose and xanthan gums, e.g. Kelzan), and swelling agents and clays such as bentonite, attapulgite and silica. Antifreezes, such as propylene glycol, and antifoams, such as the silicon antifoams, may together make up 5 to 15% w/v of the composition. Suitably about 1% w/v of a preservative, such as a biocide, may also be added.

The suspension may conveniently be prepared by premixing the pesticide (i) and other optional pesticide or pesticides with water, antifoam and the component (c) dispersant, bead milling the premix to form a 50% w/w aqueous mill base, and then incorporating the other components. Preferably the component (d) dispersant is incorporated before the bioenhancing adjuvant, component (b).

In one particular aspect of the invention there is provided an aqueous suspension of picoxystrobin which comprises:
a) approximately 25% w/v of picoxystrobin,
b) approximately one half the weight % of component (a) of a non-ionic ethoxylate surfactant,
c) approximately one tenth the weight % of component (a) of a naphthalene sulphonate-formaldehyde condensate,
d) 0.1 to 0.9% w/v of a non-ionic polymethyl methacrylate-polyethylene oxide graft copolymer,
e) 5 to 15% w/v of other additives, and
f) water in sufficient amount to bring the total composition to 100% w/v.

In another aspect of the invention there is provided an aqueous suspension of picoxystrobin which comprises:
a) approximately 25% w/v of a mixture of picoxystrobin and hexaconazole in approximately equal parts by weight,
b) one quarter to one half the weight % of component (a) of a non-ionic ethoxylate surfactant,
c) approximately one tenth the weight % of component (a) of a naphthalene sulphonate-formaldehyde condensate,
d) 0.1 to 0.9% w/v of a non-ionic polymethyl methacrylate-polyethylene oxide graft copolymer,
e) 5 to 15% w/v of other additives, and
f) water in sufficient amount to bring the total composition to 100% w/v.

The invention is illustrated with reference to the following Examples.

EXAMPLE 1

For each of a number of different batches of picoxystrobin two aqueous suspensions (identified as 'A' and 'B') were prepared according to the following recipes.

| Ingredient | Function | A (g/liter) | B (g/liter) |
| --- | --- | --- | --- |
| Picoxystrobin* | Active ingredient (Component a) | 250 | 250 |
| Morwet D425 | Sodium naphthalene sulphonate-formaldehyde condensate dispersant (Component c) | 25 | 25 |
| Atlox 4913 | Non-ionic polymethyl methacrylate-polyethylene glycol graft copolymer (Component d) | 10 | — |
| Tween 20 | Ethoxylated sorbitan monolaurate bioenhancing adjuvant (Component b) | 125 | 125 |
| Bentopharm | Antisettling agent (Component e) | 15 | 15 |
| Kelzan | Antisettling agent (Component e) | 2.5 | 2.5 |
| Proxel GXL | Biocide preservative (Component e) | 1 | 1 |
| Silcolapse M5020 | Antifoam (Component e) | 10 | 10 |
| Propylene glycol | Antifreeze (Component e) | 80 | 80 |
| Water | (Component f) | to 1 liter | to 1 liter |

*Picoxystrobin is the common name for the strobilurin plant fungicide methyl (E)-2-{2-[6-(trifluoromethyl)pyrid-2-yloxymethyl]-phenyl}-3-methoxyacrylate which is described in EP-A-0278595 (Compound No. 177 of Table I). Compositions of picoxystrobin with a variety of other fungicides are described in Research Disclosures RD 40585 (January 1998) and RD429035 (January 2000)

Suspension A illustrates the ivention. Susoension B lacks component (d) and is included for comparative purposes only.

The suspensions were prepared as follows.

Method

The picoxystrobin, antifoam, Morwet D425 and water were mixed in a high shear vortex mixer to form a 50% (500 g/kg) premix. The premix was passed through a bead mill to form a 50% (500 g/kg) picoxystrobin mill base suspension of fine particle size, approximately 70% finer than 2 μm. The remaining ingredients, except for the Tween 20, were stirred into the mill base using a vortex mixer. Tween 20 and sufficient water to bring the total suspension to 1 liter were subsequently added.

| Batch of picoxystrobin | Casson Viscosity (mPas) | |
|---|---|---|
| | Suspension B | Suspension A |
| 1 | 53 | 28 |
| 2 | 43 | 37 |
| 3 | 142 | 44 |
| 4 | 56 | 41 |
| 5 | 211 | 37 |
| 6 | 42 | 44 |
| 7 | 75 | 33 |

EXAMPLE 2

This Example shows how the use of small amounts of component (d) reduce or eliminate pre-shear thickening. Pre-shear thickening goes hand in hand with variable viscosity. Thus, formulations which exhibit pre-shear thickening also give rise to inconsistencies in viscosity. Pre-shear thickening is, therefore, a useful indicator of viscosity variability.

The pre-shear thickening was measured of formulations of (I) picoxystrobin, (II) picoxystrobin and hexaconazole, and (III) picoxystrobin and cyproconazole containing no component (d) and also with varying, small amounts of component (d) (here Atlox 4913). The measurements were carried out using a standard concentric cylinder rheology instrument, in this case a Paar Physica MC1 rotational rheometer. A sample of each of the aqueous suspension concentrates detailed below was pre-sheared for 5 minutes at a constant shear rate of 573/s using the rheometer. This ensured a uniform, homogenous product. From viscosity measurements taken at the start and finish of the pre-shearing, viscosity increases were calculated and expressed as a percent pre-shear thickening. The results are given in the tables below. Negative values indicate shear thinning.

(I) Picoxystrobin

The percentage increase in pre-shear thickening was measured on formulations (A) and (B) from Example 1, and for three other formulations the same as formulation (A) except that the amount of Atlox 4913 used was 3, 20 and 30 g/liter instead of 10 g/liter in the case of (A). The results were as follows.

| | Formulation B (Ex. 1) | Formulation A (Ex. 1) | | | |
|---|---|---|---|---|---|
| Atlox 4913 (g/l) | 0 | 3 | 10 | 20 | 30 |
| % increase in pre-shear viscosity | 15 | 9 | 2 | −2 | −1 |

Formulation A (10 g/l Atlox 4913), which showed only a small % increase in pre-shear thickening, gave a satisfactory product in terms of consistency of viscosity (see Example 1).

(II) Picoxystrobin/Hexaconazole

The percentage increase in pre-shear thickening was measured on the following formulations in which the amount of Atlox 4913 was varied between 0 and 30 g/liter.

| Ingredient | Function | (g/liter) |
|---|---|---|
| Picoxystrobin | Active ingredient (Component a) | 125 |
| Hexaconazole | Active ingredient (Component a) | 125 |
| Morwet D425 | Sodium naphthalene sulphonate-formaldehyde condensate dispersant (Component c) | 25 |
| Atlox 4913 | Non-ionic polymethyl methacrylate-polyethylene glycol graft copolymer (Component d) | 0 to 30 (see below) |
| Brij 96 | Fatty alcohol ethoxylate bioenhancing adjuvant (Component b) | 125 |
| Bentopharm | Antisettling agent (Component e) | 20 |
| Kelzan | Antisettling agent (Component e) | 2.1 |
| Proxel GXL | Biocide preservative (Component e) | 1 |
| Silcolapse M5020 | Antifoam (Component e) | 2.75 |
| Silcolapse M430 | Antifoam (Component e) | 0.042 |
| Propylene glycol | Antifreeze (Component e) | 50 |
| Water | (Component f) | to 1 liter |

The results were as follows.

| Amount of Atlox 4913 (g/l) | % Pre-shear Thickening |
|---|---|
| 0 | 4 |
| 3 | 1 |
| 6 | −4 |
| 9 | −6 |
| 10 | −2 |
| 15 | −6 |
| 27 | −7 |
| 30 | −6 |

The formulation that contained no Atlox 4913 showed pre-shear thickening. This was almost eliminated by including 3 g/liter of Atlox 4913 (0.3% w/v, equivalent to 0.1% w/v component (d)), and completely eliminated by including 6 g/liter of Atlox 4913 (0.6% w/v, equivalent to 0.2% w/v component (d)). Adding larger amounts of Atlox 4913 resulted in shear thinning which is also an indicator of consistent viscosity.

(III) Picoxystrobin/cyproconazole

The percentage increase in pre-shear thickening was measured on the following formulations in which either Brij 96 or Tween 20 was used as the bioenhancing adjuvant and the amount of Atlox 4913 was varied between 0 and 10 g/liter.

| Ingredient | Function | (g/liter) |
|---|---|---|
| Picoxystrobin | Active ingredient (Component a) | 200 |
| Cyproconazole | Active ingredient (Component a) | 80 |
| Morwet D425 | Sodium naphthalene sulphonate-formaldehyde condensate dispersant (Component c) | 28 |
| Atlox 4913 | Non-ionic polymethyl methacrylate-polyethylene glycol graft copolymer (Component d) | 0 to 10 (see below) |

-continued

| Ingredient | Function | (g/liter) |
|---|---|---|
| Tween 20 or Brij 96 | Ethoxylate bioenhancing adjuvant (Component b) | 125 |
| Bentopharm | Antisettling agent (Component e) | 10 |
| Kelzan | Antisettling agent (Component e) | 2.32 |
| Proxel GXL | Biocide preservative (Component e) | 1.7 |
| Antifoam MSA | Antifoam (Component e) | 7 |
| Silcolapse M5020 | Antifoam (Component e) | 2.8 |
| Propylene glycol | Antifreeze (Component e) | 50 |
| Water | (Component f) | to 1 liter |

The results were as follows.

| Amount of Atlox 4913 (g/l) | % Pre-shear Thickening | |
|---|---|---|
| | 125 g/l Brij 96 | 125 g/l Tween 20 |
| 0 | 21 | 18 |
| 3 | 13 | 9 |
| 6 | 4 | 2 |
| 9 | −6 | 1 |
| 10 | −5 | 1 |

The formulations that contained no Atlox 4913 showed pre-shear thickening. This was reduced by including Atlox 4913 and eliminated or reduced to a very acceptable level by including 9 g/liter of Atlox 4913 (0.9% w/v, equivalent to 0.3% w/v component (d)).

The invention claimed is:

1. An aqueous suspension of a pesticide which comprises:
   a) 5 to 40% w/v of strobilurin fungicide or (ii) a mixture of strobilurin fungicide and one or more other pesticides having a melting point of at least 50° C. and a solubility in water of not more than 0.2% w/v in the ratio of at least 1 part by weight of strobilurin fungicide to 10 parts by weight of the other pesticide or pesticides,
   b) 2.5 to 20% w/v of a non-ionic alkoxylate surfactant,
   c) 0.5 to 5% w/v of a naphthalene sulphonate-formaldehyde condensate,
   d) 0.1 to 5% w/v of a non-ionic polymethyl methacrylate-polyethylene oxide graft copolymer,
   e) 0 to 25% w/v of other additives, and
   f) water in sufficient amount to bring the total composition to 100% w/v.

2. A suspension according to claim 1 wherein component (b) is a non-ionic ethoxylate surfactant.

3. A suspension according to claim 2 wherein component (b) is a sorbitan ester ethoxylate.

4. A suspension according to claim 1 wherein component (d) has a molecular weight of 20,000 to 30,000.

5. A suspension according to claim 1 wherein component (e) comprises one or more of an antisettling agent, a preservative, an antifoam agent and antifreeze agent.

6. An aqueous suspension of a pesticide which comprises:
   a) 5 to 40% w/v of i) picoxystrobin or (ii) a mixture of picoxystrobin and one or more other pesticides having a melting point of at least 50° C. and a solubility in water of not more than 0.2% w/v in the ratio of at least 1 part by weight of picoxystrobin to 10 parts by weight of the other pesticide or pesticides,
   b) 2.5 to 20% w/v of a non-ionic alkoxylate surfactant,
   c) 0.5 to 5% w/v of a naphthalene sulphonate-formaldehyde condensate,
   d) 0.1 to 5% w/v of a non-ionic polymethyl methacrylate-polyethylene oxide graft copolymer,
   e) 0 to 25% w/v of other additives, and
   f) water in sufficient amount to bring the total composition to 100% w/v.

7. A suspension according to claim 6 wherein component (a) is a mixture of picoxystrobin and wherein the pesticide is a fungicide selected from the group comprising hexaconazole, tebuconazole, cyproconazole, quinoxyfen, epoxiconazole, cyprodinil, azoxystrobin, chlorothalonil and fluazinam.

8. A suspension according to claim 6 wherein component (a) is a mixture of picoxystrobin and hexaconazole in the ratio of 1:25 to 2:1 parts by weight.

9. A suspension according to claim 6 wherein component (b) is a non-ionic ethoxylate surfactant.

10. A suspension according to claim 9 wherein component (b) is a sorbitan ester ethoxylate.

11. A suspension according to claim 6 wherein component (d) has a molecular weight of 20,000 to 30,000.

12. A suspension according to claim 6 wherein component (e) comprises one or more of an antisettling agent, a preservative, an antifoam agent and antifreeze agebt.

13. A suspension according to claim 6 which comprises:
   a) approximately 25% w/v of picoxystrobin,
   b) approximately one half the weight % of component (a) of a non-ionic ethoxylate surfactant,
   c) approximately one tenth the weight % of component (a) of a naphthalene sulphonate-formaldehyde condensate,
   d) 0.1 to 0.9% w/v of the non-ionic polymethyl methacrylate-polyethylene oxide graft copolymer,
   e) 5 to 15% w/v of the other additives, and
   f) water in sufficient amount to bring the total composition to 100% w/v.

14. A suspension according to claim 6 which comprises:
   a) approximately 25% w/v of a mixture of picoxystrobin and hexaconazole in approximately equal parts by weight,
   b) one quarter to one half the weight % of component (a) of a non-ionic ethoxylate surfactant,
   c) approximately one tenth the weight % of component (a) of a naphthalene sulphonate-formaldehyde condensate,
   d) 0.1 to 0.9% w/v of a non-ionic polymethyl methacrylate-polyethylene oxide graft copolymer,
   e) 5 to 15% w/v of other additives, and
   f) water in sufficient amount to bring the total composition to 100% w/v.

* * * * *